United States Patent [19]

Barnett et al.

[11] 4,335,072

[45] Jun. 15, 1982

[54] OVERHEAD CORROSION SIMULATOR

[75] Inventors: Jack W. Barnett; Roy D. Sawyer, both of Missouri City, Tex.

[73] Assignee: Nalco Chemical Company, Oak Brook, Ill.

[21] Appl. No.: 293,620

[22] Filed: Aug. 17, 1981

[51] Int. Cl.$^3$ .................. G01N 17/00; C23F 14/02
[52] U.S. Cl. .................. 422/53; 23/230 C; 203/7; 422/3
[58] Field of Search .............. 422/53, 119, 3; 23/230 C, 230 A; 73/86; 203/7

[56] References Cited

U.S. PATENT DOCUMENTS

| 3,639,876 | 2/1972 | Wilson | 422/53 |
| 3,649,167 | 3/1972 | Sawyer | 422/3 |
| 3,861,876 | 1/1975 | Robertson et al. | 23/230 C |

Primary Examiner—Ronald E. Serwin
Attorney, Agent, or Firm—Lloyd L. Zickert

[57] ABSTRACT

Apparatus for determining the corrosion rate of petroleum distillation equipment so that corrosion inhibitors may be effectively utilized to control corrosion. The apparatus includes a water box having a coil arranged in the box through which hydrocarbon vapors are directed. Cooling water is forced through the box in a counterflow direction to cool the vapors and simulate cooling that will take place in heat exchange units. Corrosion and temperature probes are arranged along the coil to determine corrosion rates at the various temperature levels of the hydrocarbons so that a corrosion profile can be established and related to the temperature of the vapors at various locations in the heat exchange units of the equipment.

10 Claims, 4 Drawing Figures

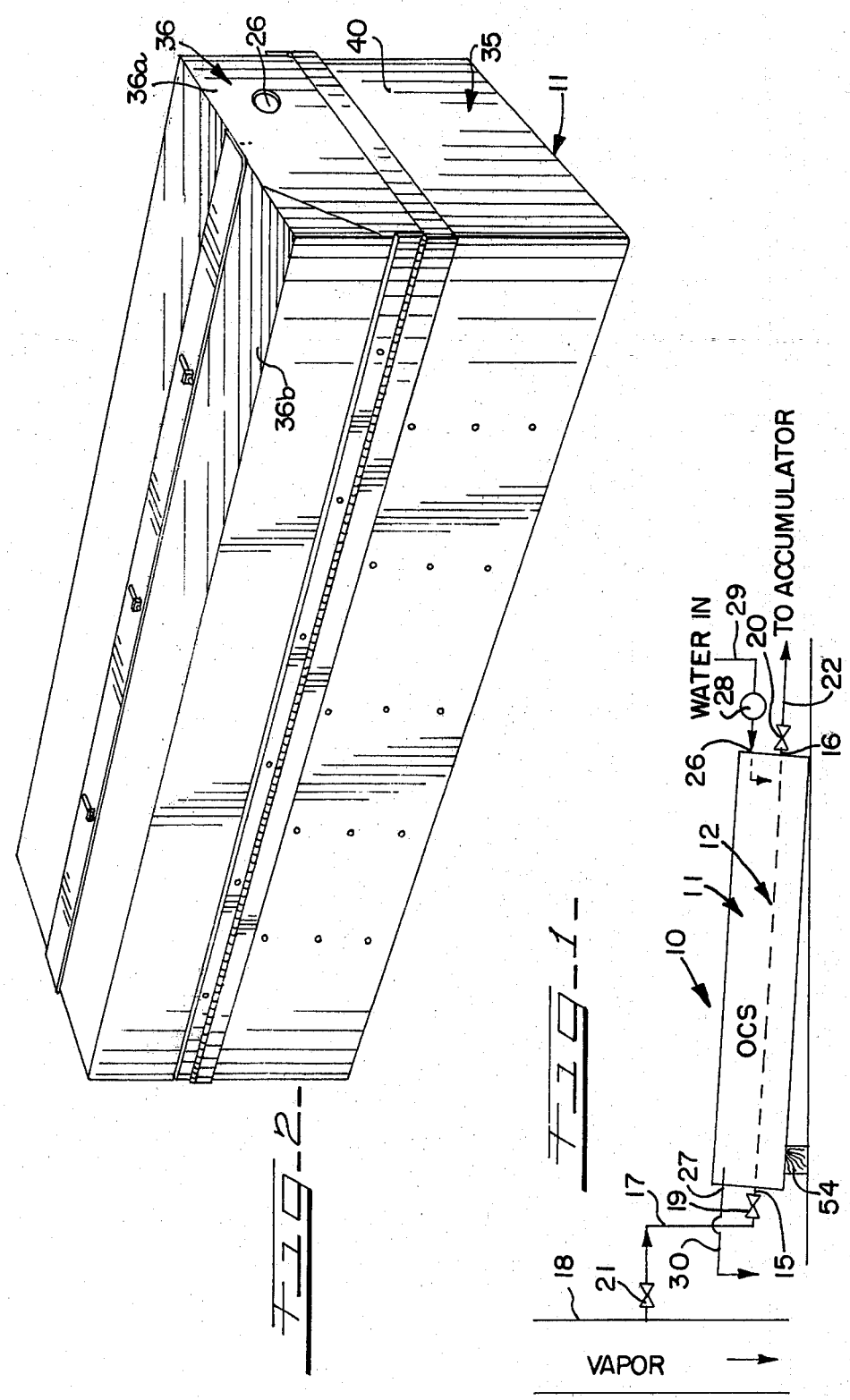

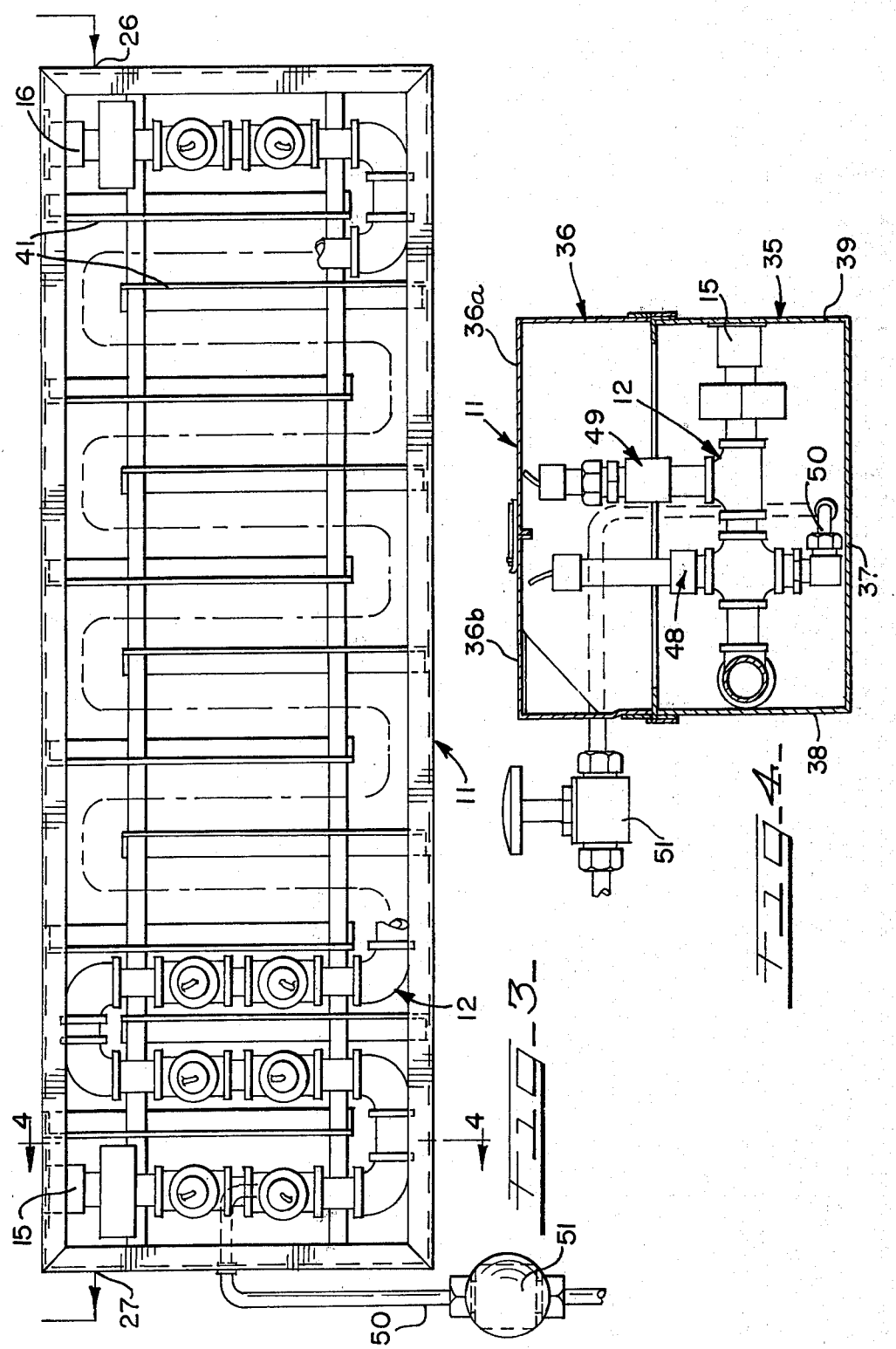

OVERHEAD CORROSION SIMULATOR

This invention relates in general to an apparatus for determining corrosion rates in petroleum distillation equipment so that corrosion inhibitors can be introduced for controlling corrosion, and more particularly to a corrosion simulator which simulates the corrosion profile of the equipment.

Crude oils are distilled in oil refinery equipment to produce various fractions such as a gasoline fraction, a fuel oil fraction or a lubricating oil fraction, and others. The fractions are cooled, condensed and sent to collecting equipment. Fractionation is accomplished by oil refining equipment which is subject to corrosion because of corroding materials that are present in the crude oils and carried along the distillation zone. Corrosion takes place on the metal surfaces of the equipment and particularly on the internal surfaces of the condensing and heat exchange units. The most serious point of aqueous corrosion activity will be near a point where water initially condenses.

Heretofore, corrosion has been detected by a number of systems and apparatuses which have considerable drawbacks in obtaining a proper corrosion profile. For example, certain equipment is inspected for corrosion by use of ultrasonic testing units which measure metal thickness through reflected sound waves. This manner of determining corrosion is limited in that most failures in refinery equipment occur on heat exchange equipment surfaces, such as the condenser and aerial fan tubing, and it is not possible to measure metal loss in these areas because the tube surfaces are not accessible unless the equipment is shut down.

Weight loss coupons have been used to detect metal loss rates where the coupons are placed in the process stream. The data generated with such a coupon system only represents corrosion at the point in the system where the coupon is located. In order to utilize corrosion rates to predict equipment condition, it is known that the most corrosive point in the system must be monitored, and this point is generally where the water first starts to condense which is at the water dew point. Since this location is almost always found on the tube surfaces within an exchanger or aerial fan where coupons cannot easily be located, the coupon system is not acceptable to measure corrosion at those points. Moreover, the points where water first condenses change with time, and a fixed location of a coupon would therefore be worthwhile only for a limited period of time. Finally, a coupon system is not capable of identifying short upsets quickly. Electrical resistance probes have been used but are fraught with the same limitations as the retractable coupon in that they always read corrosion rates at the point in the system where it is located. However, such a probe is superior to the coupon system because it generates data more rapidly and can overcome the problem of identifying short upset conditions.

Samplings of the stream are useful in monitoring corrosion activity and in identifying upset conditions, but they cannot differentiate between extremely severe localized pitting or moderate corrosion in a system.

It has also been known to have an apparatus for measuring corrosion potential which analyzes the initial condensate situation where the temperature of the surrounding environment reaches the dew point of water, as disclosed in U.S. Pat. No. 3,649,167. However, this system will not indicate metal loss or corrosion activity.

The present invention overcomes the problems heretofore encountered in measuring corrosion in petroleum distillation equipment in that it can quickly and accurately measure the rate of corrosion which is present at any point in an overhead system, thereby monitoring and optimizing a process control program. The invention comprises an overhead corrosion simulator which is a miniature overhead system that simulates the corrosion environment present on the condensor surfaces in the process unit being monitored. The simulator takes a slip stream of the hydrocarbon vapors at a temperature considerably higher than the dew point temperature of the water in the stream and cools the stream and measures the corrosion rate over the range of temperature differential above and below the dew point temperature. Corrosion rates at various temperatures are determined to provide a corrosion profile of the equipment so that corrosion inhibitors can be injected at the proper locations in order to reduce corrosion for the particular vapor stream encountered. Electrical resistance probes can be used to measure corrosion activity. In addition to measuring corrosion, the simulator of the present invention can be used to measure elemental hydrogen release from corrosion reactions where a hydrogen blistering action would be probable in order to counteract such action. Coupons can also be used in the simulator to measure corrosion especially where generalized corrosion conditions exist. In predominantly aqueous phase systems, polar probes such as those used in cooling water programs can be used to measure corrosion potential. It should also be appreciated that the simulator can be equipped with any combination of corrosion measuring devices depending upon the needs. Temperature measuring probes are also used to measure the temperature at the various points in the simulator so as to correlate temperature versus corrosion rates. Further, sampling lines may be provided at various points along the coil for extracting samples of condensate to make other suitable tests helpful to implement a corrosion-prevention program.

It is therefore an object of the present invention to provide a new and improved apparatus for quickly and accurately measuring corrosion rate present at any point in oil refinery equipment in order to promptly and effectively enhance the institution of corrosion control.

Another object of the present invention is in the provision of a corrosion simulator for oil refinery equipment to simulate the corrosion environment present on condenser or heat exchanger surfaces used in the equipment.

A still further object of the present invention resides in the provision of a corrosion simulator for oil refinery equipment that is capable of measuring corrosion occurring on the inner metal surfaces of heat exchange units, which includes a water box having a coil therein through which a stream of hydrocarbon vapors is directed and cooled and wherein a plurality of corrosion and temperature detectors are mounted at points along the coil to detect corrosion occurring at different temperatures so that a temperature-corrosion profile can be obtained.

BRIEF DESCRIPTION OF THE DRAWINGS

Other objects, features and advantages of the invention will be apparent from the following detailed disclosure, taken in conjunction with the accompanying sheets of drawings, wherein like reference numerals refer to like parts, in which:

FIG. 1 is a diagrammatic view of the overhead corrosion simulator of the invention illustrating the hookup to the overhead vapor line and to the cooling water;

FIG. 2 is a perspective view of the water box which contains the coil and the measuring probe;

FIG. 3 is a top plan view of the coil situated in the water box where the cover members to the water box have been removed for purposes of clarity; and FIG. 4 is a vertical sectional view taken through the water box and the coil substantially along line 4—4 of FIG. 3 but also showing the cover members in closed position.

Referring now to the drawings, and particularly to FIG. 4, the overhead corrosion simulator of the invention, generally designated by the numeral 10, is shown as it would be hooked up to petroleum distillation equipment for purposes of monitoring and optimizing a process corrosion control program for the equipment. The simulator 10 generally includes an elongated water box 11 having a coil 12 mounted therein which takes a slip stream of hydrocarbon vapors from the overhead vapor line of a fractionation tower. Cooling water is pumped through the water box in a counter-current flow to the flow of the slip stream, thereby cooling the stream to simulate the cooling conditions encountered by the hydrocarbon vapors in the condensing and/or heat exchange units of the system. Thus, the simulator is utilized in an oil refinery or petrochemical plant so as to monitor the varying corrosion problems encountered to enable the proper introduction of corrosion inhibitors to control corrosion and enhance the life of the equipment.

The coil 12 includes an inlet 15 and an outlet 16. The inlet is connected to a line 17 coming from the overhead vapor line 18. Block valves 19 and 20 are provided at the inlet and outlet to the coil to control stream flow through the coil. Additionally, a block valve 21 is provided in the connecting line 17 at the overhead vapor line 18. It is preferable that the slip stream is taken from a vertical section of the overhead vapor line as illustrated in FIG. 1 and that the line 17 is routed to a platform as near the sample point as possible. In order to minimize cooling in the line 17, it should be insulated. Likewise, the block valves 19 and 21 should be insulated. The outlet 16 of the coil is connected to a line 22 which is preferably routed to the inlet of the overhead accumulator or to a location which will assure that there is sufficient pressure drop across the simulator to provide for proper flow of the stream through the coil. By locating the sample point in a vertical section of the overhead vapor line, that will insure that a representative sample of the overhead vapors is routed through the simulator. Moreover, it is important that the temperature of these vapors be substantially above the dew point of the water in the vapors.

Since the simulator 10 would most likely be supported on a deck where a fire water supply is available, cooling water for the simulator may be drawn from the fire water line. However, it can be appreciated that cooling water may be drawn from any suitable source. The water box 11 includes a cooling water inlet 26 and a cooling water outlet 27. Inasmuch as the pressure for a cooling water supply may tend to fluctuate, a pressure regulator 28 is placed in the cooling water inlet line 29 to help assure even cooling water flow through the water box, thereby stabilizing temperature control in the coil. Cooling water leaving the water box may be routed through the outlet line 30 to the sewer in any suitable manner. As may be appreciated by the illustrations in FIGS. 3 and 4, the coil 12 is arranged near the bottom of the water box 11. Water is introduced into the box above the coil and also removed from the box through the outlet at a location above the coil so that the coil is generally immersed in the cooling water during the flow of the water through the box.

The water box 11 is preferably made of aluminum although it could be made of any suitable material, and it includes a lower section 35 and an upper cover section 36. The lower section includes interconnecting bottom, front, back and end walls 37, 38, 39 and 40. The coil inlet and outlet are at the back wall 39. Within the lower section as shown in FIG. 3, a plurality of baffles 41 are alternately extending from the front and back walls so as to define a winding or sinusoidal path along which the cooling water must flow between the inlet 26 and the outlet 27. Likewise, the coil 12 is windingly or sinusoidally formed so as to fit within the water box and extend around the baffles 41. As will be more clearly explained, a temperature zone is defined between each adjacent pair of baffles as well as the end baffles and the end walls of the water box.

The upper cover section 36 is constructed of sections 36a and 36b for purposes of allowing suitable access to the water box. Once the cooling water inlet and outlet lines are connected, the section 36a will be maintained in place but the section 36b may be easily opened and closed for servicing of the coil. The cover sections are connected to the lower section 35 by means of suitable hinges.

The coil 12 is constructed preferably of one inch malleable cast iron pipe that is easily available from any pipe supply outlet and is formed of suitable lengths and fittings to take the shape illustrated in FIG. 3, whereby it extends through each of the baffled areas of the water box. Between each baffled area the fittings receive a temperature probe 48 and a corrosion probe 49. The temperature probe 48 may be of any suitable type such as a thermometer or thermocouple for measuring the temperature at a given temperature zone, while the corrosion probe may be of any suitable type of monitoring any particular corrosion activity. The type of corrosion probes contemplated will be set forth hereinafter. Thus, the temperature and corrosion probes are provided in sets along the water box. While twelve such sets are illustrated in the drawings, it should be appreciated that a greater or lesser number may be provided depending upon the objectives of the particular installation.

Additionally, there may be provided as illustrated at each temperature zone a sampling line 50 which includes a valve 51 that permits the taking of a sample of the process water to allow accurate measurement of process water pH, chlorides, etc. While only one such sample line is shown, it should be appreciated that they can be provided for each of the temperature zones if desired.

The coil 12 is constructed so that each of the legs defining the temperature zones is arranged in the same plane and parallel to the bottom wall of the water box. The coil 12 should be inclined from the inlet to the outlet as illustrated in FIG. 1 to insure that the hydrocarbon flow through the coil is downhill and thereby prevent the backward flow of condensed hydrocarbon and water. Only a slight incline is needed to prevent the backward flow of water. While it could be appreciated that the coil could be inclined relative the bottom of the box, it is easier to mount the coil parallel to the bottom of the box and incline the entire box as shown in FIG. 1 by use of a small block 54.

In a refinery the most severe point of aqueous corrosion attack will be near a point where water initially condenses. This point is continually moving because of changes in partial pressures of the gases, changes in gas composition and total pressure fluctuations. The simulator of the present invention can monitor the changing positions of the most severe point of corrosion attack by virtue of the several temperature zones that have been provided. Moreover, by having the various temperature zones, the rate of corrosion at any point in the overhead system can be quickly and accurately measured.

Various corrosion probes may be utilized at each temperature zone. For example, electrical resistance probes may be employed which measure corrosion rate in mils per year (MPY). Such a probe functions on the basis that the electrical resistance changes as the probe corrodes to provide a reading of corrosion rate. The electrical resistance increases as the cross-sectional area decreases, and the increased resistance can be read from a suitable recording instrument as the amount of metal lost which is easily converted to corrosion rate. One form of such a probe is made by Rohrback Instruments and marketed under the trademark Corrosometer. Another type of probe that also may be used, also made by Rohrback Instruments, which is marketed under the trademark Corrater, provides a direct indication of the corrosion rate and pitting tendency of electrically conductive liquids and which therefore measures corrosion as it occurs. In some installations, particularly where generalized corrosion exists, the corrosion probe may be of the retractable coupon type which is well known. Where hydrogen blistering is a problem, the probe may be a hydrogen probe that would measure elemental hydrogen release from corrosion reactions. It can further be appreciated that any combination of probes may be utilized in the simulator of the invention.

The placement of the temperature probe adjacent to each corrosion probe permits the correlation of temperature versus corrosion rates so as to obtain a temperature-corrosion profile. Such was not possible prior to the development of the present invention. Because the corrosion probes of the coil are in a coil that is immersed in cooling water, that point will more closely resemble the exchanger or aerial fan tube which is surrounded by a cooling media.

In operation, a slip stream of hydrocarbon vapors is drawn from the vertical leg 18 of the overhead vapor line to pass through the coil 12 of the overhead corrosion simulator. Valves 27 and 28 control the stream flow. Cooling water is introduced into the water box 11 at the inlet 26 and discharged from the box at outlet 27. Water flows in a winding path around the baffles to the outlet. The water pressure is regulated by the regulator 28 to maintain the desired level in the box at all times and so the coil remains completely immersed, thereby providing uniform cooling along the coil and stabilizing temperature control. As the water passes from one baffled area to another, it will increase in temperature. Thus, each baffled area will represent a different temperature zone or level and will be recordable by the temperature probe in that zone. Likewise, each zone will have a corrosion probe for measuring corrosion, thus providing a temperature-corrosion profile for the equipment.

After a simulator of the invention as illustrated is placed on a process unit, it should take twenty to thirty minutes to get the simulator operating in a steady state condition. Temperatures on each temperature probe should not fluctuate more than ± five degrees F. after an equilibrium condition is reached. When equilibrium is reached, each of the twelve temperature and corrosion probes should be read. The exact time should be recorded as each probe reading is taken. We have found that the W-40 Rohrback probe provides accurate corrosion readings, although other probes function suitably. Corrosion readings can be calculated for periods as short as six hours. This is particularly the case in units suffering from extremely severe corrosion, i.e., more than 100 MPY. However, it has been found that readings provide more accurate results when they are taken at least 24 hours apart. In units where corrosion is less than 10 MPY, weekly readings may be required to obtain statistically meaningful data.

Corrosion readings from a Corrosometer probe are calculated using the following formula:

$$\text{Corrosion Rate } (MPY) = \frac{\Delta \text{ Dial Reading}}{\Delta \text{ Time (Days)}} \times 0.365 \times \text{multiplier}$$

The multiplier for a W-40 probe is 10. Since the readings from the probes are taken more frequently than normal, they need to be adjusted to an hourly basis. This can be done by using the following formula:

$$\text{Corrosion Rate } (MPY) = \frac{\Delta \text{ Dial Reading}}{\Delta \text{ Time (hours/24)}} \times 0.365 \times \text{multiplier}$$

Assume the following readings were taken from one of the W-40 probes on the unit.

| Probe No. | Dial Reading | Time | Date | Temp. |
| --- | --- | --- | --- | --- |
| #4 | 210 | 10:00 am | 4/22 | 217° F. |
| #4 | 228 | 9:00 am | 4/24 | 219° F. |

$$\text{Corrosion Rate} = \frac{228 - 210}{47 \text{ hrs}/24 \text{ hrs}} \times 0.365 \times 10$$

$$= 33.5 \text{ MPY}$$

The corrosion rate on the probe was 33.5 MPY. If the readings had not been adjusted to the hour, the corrosion rate would have been 32.9 MPY.

The probes are numbered 1 to 12 to identify their location in the unit.

Data from one installation on a crude unit follows as an example. There was no ammonia in the unit except for the amount that was coming in from the desalter.

| Probe | Date | Time | Temperature | Dial | MPY | pH |
| --- | --- | --- | --- | --- | --- | --- |
| #1 | 11/3 | 11:00 | 296° F. | 113 | — | N.W. |
|  | 11/5 | 10:30 | 296° F. | 141 | 51.6 | N.W. |
| #2 | 11/3 | 11:00 | 283° F. | 176 | — | N.W. |
|  | 11/5 | 10:30 | 283° F. | 200 | 44.3 | N.W. |
| #3 | 11/3 | 11:00 | 268° F. | 156 | — | 6.8 |
|  | 11/5 | 10:30 | 272° F. | 194 | 70.1 | 6.0 |
| #4 | 11/3 | 11:00 | 255° F. | 193 | — | — |
|  | 11/5 | 10:30 | 258° F. | 236 | 79.3 | — |
| #5 | 11/3 | 11:00 | 245° F. | 230 | — | — |
|  | 11/5 | 10:30 | 250° F. | 278 | 88.5 | — |
| #6 | 11/3 | 11:00 | 238° F. | 164 | — | 6.0 |
|  | 11/5 | 10:30 | 244° F. | 208 | 81.2 | 5.0 |
| #7 | 11/3 | 11:00 | 232° F. | 188 | — | — |
|  | 11/5 | 10:30 | 238° F. | 217 | 53.5 | — |
| #8 | 11/3 | 11:00 | 218° F. | 127 | — | 5.7 |
|  | 11/5 | 10:30 | 220° F. | 149 | 40.6 | 5.0 |
| #9 | 11/3 | 11:00 | 210° F. | 155 | — | — |
|  | 11/5 | 10:30 | 217° F. | 179 | 44.3 | — |
| #10 | 11/3 | 11:00 | 205° F. | 129 | — | — |

-continued

| Probe | Date | Time | Temperature | Dial | MPY | pH |
|---|---|---|---|---|---|---|
| | 11/5 | 10:30 | 212° F. | 147 | 33.2 | 4.9 |
| #11 | 11/3 | 11:00 | 201° F. | 109 | — | 5.3 |
| | 11/5 | 10:30 | 206° F. | 127 | 33.2 | — |
| #12 | 11/3 | 11:00 | 178° F. | 212 | — | — |
| | 11/5 | 10:30 | 195° F. | 234 | 40.6 | 4.9 |
| Acc: | 11/3 | 11:00 | | | | 5.1 |
| | 11/5 | 10:30 | | | | 5.4 |

On this unit the sample point in the vapor line is located upstream of the filming inhibitor injection point. This partially explains why the corrosion readings are high. The calculated water dew point on this crude unit is 257 degrees F. But note that some water was obtained in the sample from the simulator at 268 degrees F. to 272 degrees F. This is caused by localized surface cooling on the walls of the coil. Water condenses on the tube surfaces of a condensor in a similar manner. Even though there was no measurable water present on probes 1 and 2, corrosion rates of 51.6 MPY and 44.3 MPY respectively were recorded on these probes. On this unit the No. 1 probe always read higher corrosion levels than the second probe. This is because the sample line leading from the vapor line to the simulator was not properly insulated. A very small amount of water was condensing in the sample line. This resulted in elevated first probe readings. Also, when the temperature probe housings from the hotter locations of the simulator were inspected, they were coated with some ammonium chloride even though ammonia was not supposed to be in the unit.

From the foregoing it can be appreciated that the present invention permits the quick and accurate measurement of corrosion activity on the internal surfaces of condensing and exchange equipment in an oil refinery or petrochemical plant so that a corrosion control program can be optimally carried out.

It will be understood that modifications and variations may be effected without departing from the scope of the novel concepts of the present invention, but it is understood that this application is to be limited only by the scope of the appended claims.

The invention is hereby claimed as follows:

1. In a petroleum refinery having a fractionation tower interconnected by an overhead vapor line to condensing and/or heat exchange equipment, an overhead corrosion simulator for simulating and measuring the corrosion activity on the internal surfaces of said equipment, said simulator comprising a water box having a cooling coil therein, said coil having an inlet connected to said overhead vapor line to take a slip stream of hydrocarbon vapors at a temperature substantially higher than the dew point of water in the stream, and an outlet connected to a point in the refinery such that a sufficient pressure drop is established across the simulator to assure movement of the stream through the coil, said water box having an inlet and an outlet for cooling water to cause counterflow to the stream, and a plurality of corrosion probes mounted along the coil to measure corrosion rate of the stream at various temperatures.

2. The simulator defined in claim 1, which further includes a temperature probe at each corrosion probe for measuring the temperature at the corrosion probe and provide a temperature-corrosion profile for the condensing and/or heat exchange equipment.

3. The simulator defined in claim 1, which further includes a sampling line at each corrosion probe for taking a sample to measure chlorides and/or pH.

4. The simulator defined in claim 2, which further includes means for regulating the stream flow, and means for regulating the water supply to the water inlet to coact with the means for regulating the stream flow and thereby regulate the temperature of the stream along the coil.

5. The simulator defined in claim 4, wherein the coil is inclined downward from the inlet to the outlet.

6. The simulator defined in claim 5, which further includes a sampling line at each corrosion probe for taking a sample to measure chlorides and/or pH.

7. Apparatus for simulating and measuring corrosion activity on the internal surfaces of condensing and/or heat exchange devices in a petroleum refinery system having a fractionation tower overhead vapor line, said apparatus comprising, a water box having a cooling coil therein, said coil having an inlet connected to the overhead vapor line to take a slip stream of hydrocarbon vapor at a temperature substantially higher than the dew point of water in the stream, and an outlet connected to the system, means for regulating the stream flow, said water box having an inlet and outlet for cooling water the flow of which is counter to the stream flow, means for providing a regulated water supply to the water inlet to coact with the means for regulating the stream flow and thereby regulate the temperature of the stream along the coil, and a plurality of temperature and corrosion probes mounted in sets along the coil to measure temperature and corrosion and provide a temperature-corrosion profile for the condensing and/or heat exchange devices.

8. The apparatus defined in claim 7, wherein the coil is inclined downward from the inlet to the outlet.

9. The apparatus defined in claim 8, which further includes a sampling line at each set of temperature and corrosion probes for taking a sample to measure chlorides and/or pH.

10. The apparatus defined in claim 8, wherein the water box includes a plurality of baffles alternately disposed to provide adjacent and interconnected compartments defining a winding or sinusoidal path for the cooling water, and said coil having a plurality of interconnected legs one in each compartment, wherein a temperature and a corrosion probe is mounted on each leg.

* * * * *